United States Patent [19]

Valdiserri

[11] 4,287,339
[45] Sep. 1, 1981

[54] PHOSPHITE-ISOCYANURATES

[75] Inventor: Leo L. Valdiserri, Belpre, Ohio

[73] Assignee: Borg-Warner Corporation, Chicago, Ill.

[21] Appl. No.: 126,142

[22] Filed: Feb. 29, 1980

[51] Int. Cl.³ ............................................ C07D 251/34
[52] U.S. Cl. ................................................... 544/214
[58] Field of Search ........................................ 544/214

[56] References Cited

U.S. PATENT DOCUMENTS

| 4,085,283 | 4/1978 | Den Otter et al. | 544/214 |
| 4,096,114 | 6/1978 | Minagawa et al. | 544/214 |

FOREIGN PATENT DOCUMENTS

| 54-25951 | 2/1979 | Japan . |
| 54-30241 | 3/1979 | Japan . |
| 1526603 | 9/1978 | United Kingdom . |

Primary Examiner—John M. Ford
Attorney, Agent, or Firm—Joseph Shekleton

[57] ABSTRACT

This invention of the present application relates to the stabilizing component in the stabilization of olefin polymers, especially polypropylene during processing, i.e., at elevated temperatures. The stabilizing component is a phosphite-isocyanurate compound having the structural formula:

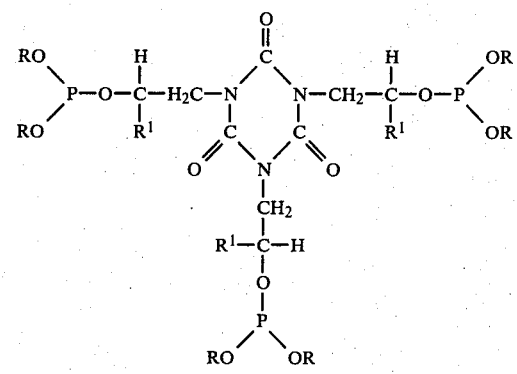

wherein R is a hydrocarbon radical and $R^1$ is methyl or hydrogen.

4 Claims, No Drawings

PHOSPHITE-ISOCYANURATES

This invention relates as indicated to stabilized polymer compositions. More particularly it relates to such compositions wherein the stabilizing component is a phosphite isocyanurate compound. Still more particularly it relates to the stabilization of olefin polymers, especially polypropylene, during processing, i.e., at elevated temperatures.

Olefin polymers are used in a wide variety of applications including wire and cable insulation, luggage, television and radio cabinets, hospital equipment, and the like. In all of such uses, however, it is necessary first that the polymer be melted as in an extruder and then extruded through a suitably shaped die. The extrudate is chopped to a powder, in which form it is available for injection molding, etc.

The temperatures of such processing operations are quite high, e.g., 235°–275° C., high enough to give rise to a problem of thermal stability. At these temperatures the olefin polymer tends to undergo oxidation and becomes discolored. It also undergoes a certain degree of chain scission.

Japanese Pat. No. 79/30241 shows polyethylene and polypropylene compositions containing 2,2',2"-((1,3,5-s-triazine-2,4,6-[1H,3H,5H]-trionyl)tris[ethylene bis-(alkylphenyl)]phosphites.

The stabilization of synthetic resins in general by the presence of a small proportion of bis-(2,4,-ditertiarybutylphenyl)pentaerythritol diphosphite or bis-(2,tertiarybutyl-5-methylphenyl)pentaerythritol diphosphite is shown in published Japanese application No. 79/25,951. Polyethylene stabilized in this fashion is shown. The stabilized compositions also contain calcium stearate, pentaerythritol tetrakis(3,5-ditertiarybutyl-4-hydroxyphenyl propionate) and dilauryl thiodipropionate.

U.K. Pat. No. 1,526,603 shows the use of bis-(alkylphenyl)pentaerythritol diphosphites as stabilizers for polypropylene. The bis-(2,4-ditertiarylbutylphenyl)pentaerythritol diphosphite is shown specifically, in combination with calcium stearate and tetrakis-[methylene-3-(3',5'-ditertiarybutyl-4'-hydroxyphenyl)propionate]methane.

The invention of the present application is a polymer composition comprising a major proportion of polymer and a minor proportion, sufficient to improve the processing stability of the polymer, of a phosphite-isocyanurate compound having the structural formula

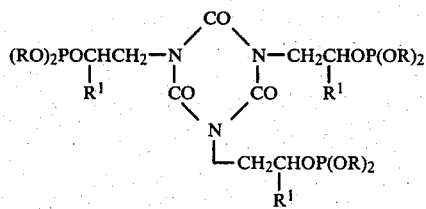

where R is a hydrocarbon radical and $R^1$ is methyl or hydrogen. Preferably, the polymer is an olefin polymer.

Preferred hydrocarbon radicals (for R in the above formula) include aromatic, aliphatic and cycloaliphatic radicals. Illustrative species include aromatic hydrocarbon radicals such as phenyl, 1-naphthyl, p-cresyl, o-cresyl, 4-tertiarybutylphenyl, 2,4-ditertiarybutylphenyl, 2-methyl-4-tertiary-butylphenyl and 2,4-diisopropylphenyl; aliphatic radicals such as methyl, ethyl, n-propyl, tertiarybutyl, n-butyl, n-octyl, isodecyl and n-dodecyl and n-dodecyl; and cycloaliphatic hydrocarbon radicals such as cyclopentyl, cyclohexyl, 2-methylcyclohexyl, 2,4-dimethylcyclohexyl and 2-methylcyclopentyl. The two R radicals may be connected by a bridging group, e.g., alkylene, O or S. The two R radicals may be the same or different.

The above composition is relatively stable at elevated temperatures, i.e., its melt viscosity remains fairly constant and its color virtually unchanged.

Olefin polymers are characterized for the most part by a relatively low density. They are wax-like in appearance, and are very inert chemically. Other polymers contemplated herein include polycarbonates, vinyl chloride polymers, styrenics, phthalic acid esters, etc.

The concentration of phosphite in the polymer composition ranges from about 0.01 to about 1.0 pph (parts per hundred parts of olefin polymer).

The olefin polymer compositions of the invention may also contain a phenolic antioxidant, which acts to enhance the effectiveness of the phosphite additive. Illustrative phenolic compounds include phenolic esters, especially esters of 3-(3',5'-ditertiarybutylphenyl)-propionic acid such as the stearyl, lauryl, ethylene, trimethylene, propylene, 1,2-hexylene, neopentyl, glyceryl and pentaerythritol esters, i.e., those having a molecular weight greater than about 425; substituted phenols and naphthols wherein the phenolic group is "hindered" by a bulky group, e.g. tertiary butyl, tertiary amyl, cyclohexyl and the like, in the ortho position, such as butylated hydroxytoluene (BHT), 2-teriarybutyl-1-naphthol, o-cyclohexylphenol, o-tertiarybutylphenol, etc.

The amount of phenolic antioxidant to be used in these compositions will range from about 0.01 to about 1.0 pph.

Other types of well-known polymer additives may also be used in the polymer compositions of this invention for their known purposes, including particularly metal carboxylates such as calcium stearate, cadmium stearate, zinc laurate and the like.

The phosphite-isocyanurate compounds of the present invention may be prepared in a variety of ways, all utilizing a tris-(hydroxyalkyl)isocyanurate as a starting material. It may be reacted with a tertiary phosphite, or with a chlorophosphite, i.e., a diorganochlorophosphite where the organo groups are hydrocarbon, or with a phosphormonoamidite.

Illustrative methods of preparation are as follows:

EXAMPLE I

A mixture of 10.44 grams (0.0335 mol) of tris-(hydroxyethyl)isocyanurate, 60 grams (0.2400 mol) of tri-n-butyl phosphite and 0.1 gram of 1,8-bis-(dimethylamino)naphthalene is heated at 100° C. with stirring in a nitrogen atmosphere for one hour, then at reduced pressure to remove by-product n-butanol. The temperature is raised gradually to 175° C./0.1 mm. The residue is dissolved in heptane, filtered through a silicèous filter aid and concentrated to a viscous, pale yellow liquid, identified by elemental analyses, liquid chromatography and NMR as the desired 2,2',2"-(1,3,5-S-triazine-2,4,6[1H,3H,5H]-trionyl)tris(ethyl dibutyl phosphite).

EXAMPLE II

A solution of 23 grams (0.05 mol) of bis-(2,4-ditertiarybutylphenyl)phosphite, 4.13 grams (0.015 mol) of tris-(hydroxyethyl)isocyanurate and a trace of triethylamine in 100 ml. of acetonitrile is heated at reflux temperature for one hour, filtered while hot, and then allowed to cool. The filtrate is concentrated by distillation and the residue identified as the desired 2,2',2''-(1,3,5-s-triazine-2,4,6[1H,3H,5H]-trionyl)tris[ethyl bis-(2,4-ditertiarybutylphenyl)phosphite], by means of elemental analysis, infra red, SEC (steric exclusion chromatography) and NMR (nuclear magnetic resonance).

EXAMPLE III

A solution of 25.8 (6.082 mol) of di-(2-methycyclohexyl)chlorophosphite in 100 ml. of benzene is added to a solution of 7.0 grams (0.025 mol) of tris-(hydroxyethyl)isocyanurate in 20.2 grams (0.200 mol) of triethylamine and the resulting mixture stirred for 16 hours at room temperature. It then is heated to reflux temperature and filtered and the filtrate stripped. An infra red spectrum of the residue shows that the reaction is not complete, so an additional 1.15 grams of di-(2-methylcyclohexyl)chlorophosphite dissolved in 25 ml. of triethylamine is added and this mixture heated to reflux and filtered. The filtrate is concentrated to a viscous, liquid residue which is identified by means of NMR and elemental analyses as consisting principally of the desired 2,2',2''-(1,3,5-s-triazine-2,4,6[1H,3H,5H]-trionyl)tris-(ethyl bis-(2-methylcyclohexyl)phosphite.

EXAMPLE IV

A mixture of 27.9 grams (0.1 mol) of tris-(hydroxyethyl)isocyanurate, 62 grams (0.5 mol) of trimethyl phosphite and 0.1 gram of 1,8-bis-(dimethylamino)naphthalene is heated so as to drive off by-product methanol. When about two-thirds of the theoretical amount of methanol has been recovered, an additional 37.2 grams (0.3 mol) of trimethyl phosphite is added and the mixture is stripped to 110° C. under reduced pressure. The residue, upon titration with iodine, is shown to consist of 96% of phosphite.

The stability of the polypropylene compositions herein is shown by data obtained from a Multiple-Extrusion test. The data is shown in Table I. The test involves extruding into a 25-mil sheet a sample of the blended polymer composition at 525° F., and measuring the Melt Index (M.I.) (ASTM 1238-L) of the extrudate. This process is repeated five times.

Each of the test samples in the Table contains polypropylene plus 0.1 phr calcium stearate plus 0.1 phr tetrakis-[methane 3-(3',5'-ditertiarybutyl-4'-hydroxyphenyl)propionate]methane plus 0.1 phr phosphite, as indicated.

TABLE

| Phosphite | M.I. (Extruder Passes at 525° F.) | | | | |
|---|---|---|---|---|---|
| | 1 | 2 | 3 | 4 | 5 |
| none | 5.5 | 6.7 | 8.0 | 8.4 | 10.9 |
| Product of Ex. 1 | 3.2 | 3.7 | 3.9 | 4.4 | 4.5 |
| Product of Ex. 2 | 4.6 | 4.8 | 5.8 | 7.2 | 6.9 |
| Product of Ex. 3 | 3.8 | 3.7 | 4.1 | 4.8 | 5.7 |

I claim:

1. A phosphite-isocyanurate compound having the structural formula

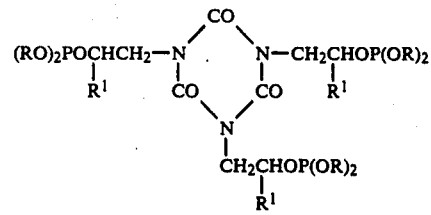

where R is a hydrocarbon radical having 1–14 carbon atoms and $R^1$ is methyl or hydrogen.

2. The phosphite-isocyanurate compound of claim 1 wherein $R^1$ is hydrogen.

3. The phosphite-isocyanurate compound of claim 1 wherein R is an aromatic hydrocarbon radical.

4. The phosphite-isocyanurate compound of claim 1 wherein R is an aliphatic hydrocarbon radical.